United States Patent [19]

Yoshida et al.

[11] Patent Number: 5,051,355
[45] Date of Patent: Sep. 24, 1991

[54] ANTI-HUMAN GASTRIC CANCER MONOCLONAL ANTIBODY

[75] Inventors: Hajime Yoshida, Sagamihara, Japan; Nobuo Hanai, Mercer Island, Wash.; Akiko Furuya, Machida, Japan

[73] Assignee: Kyowa Hakko Kogyo Co., Ltd., Tokyo, Japan

[21] Appl. No.: 445,160

[22] Filed: Dec. 6, 1989

Related U.S. Application Data

[63] Continuation of Ser. No. 70,071, Jul. 6, 1987, abandoned.

[30] Foreign Application Priority Data

Jul. 15, 1986 [JP] Japan ................................. 61-166138

[51] Int. Cl.$^5$ .................. G01N 33/53; G01N 33/567; C07K 15/14; C12N 15/00
[52] U.S. Cl. ..................................... 435/7.23; 435/7.1; 435/7.9; 435/7.92; 435/7.94; 435/172.2; 435/240.27; 436/501; 436/503; 436/536; 436/548; 436/540; 436/64; 436/813; 530/387; 530/809; 935/95; 935/103; 935/106; 935/110

[58] Field of Search ..................... 435/7, 172.2, 240.27, 435/7.1, 7.23, 7.5, 7.9, 7.92, 7.94; 436/501, 503, 518, 548, 813, 536, 538, 540, 64; 530/395, 387, 809; 935/103, 110, 95, 106

[56] References Cited

FOREIGN PATENT DOCUMENTS 00758  3/1984  World Int. Prop. O. .
86/00414  1/1986  World Int. Prop. O. .

OTHER PUBLICATIONS

Del Villano et al., Clin. Chem., vol. 29, No. 3 (1983), 549:52.
Metzgar et al., P.N.A.S., vol. 81 (1984), 5242:46.
Imai et al., J. Immun., vol. 132, No. 6 (1984), 2992:97.

Primary Examiner—Esther L. Kepplinger
Assistant Examiner—Florina B. Hoffer
Attorney, Agent, or Firm—Fitzpatrick, Cella, Harper & Scinto

[57] ABSTRACT

An anti-human gastric cancer monoclonal antibody, AMC-462, which belongs to the class IgG$_1$, reacts with human digestive system cancer, and recognizes sialylated glycoproteins or glycolipids as the antigen is disclosed. It is effective for diagnosis of digestive system cancer, especially pancreatic cancer.

6 Claims, 4 Drawing Sheets

FIG. 1

ANTIGENS DETECTED BY AMC—462 (u/ml)

| POSITIVE RATE | | <10 | 10 | 50 | 70 | 100 | 500 | 1000 | >1000 |
|---|---|---|---|---|---|---|---|---|---|
| 0% | NORMAL HUMAN (85) | | | | | | | | |
| 18.6% | GASTRIC CANCER (86) | | | | | | | | |
| 81.8% | PANCREATIC CANCER (22) | | | | | | | | |
| 33.3% | LIVER CANCER (15) | | | | | | | | |
| 6.7% | COLON CANCER (16) | | | | | | | | |
| 0% | RECTAL CANCER (12) | | | | | | | | |
| 40% | GALL BLADDER CANCER (20) | | | | | | | | |
| 33.3% | BREAST CANCER (3) | | | | | | | | |
| 0% | MISCELLANEOUS CANCER (10) | | | | | | | | |
| 0% | BENIGN GALL BLADDER DISEASES (11) | | | | | | | | |
| 0% | LIVER CIRRHOSIS (3) | | | | | | | | |
| 0% | BENIGN GASTROINTESTINAL DISEASES (21) | | | | | | | | |
| 2.6% | BENIGN PANCREATIC DISEASE (38) | | | | | | | | | ial.
ANTI-HUMAN GASTRIC CANCER MONOCLONAL ANTIBODY

This application is a continuation of application Ser. No. 070,071 filed July 6, 1987, now abandoned.

BACKGROUND OF THE INVENTION

The present invention relates to a monoclonal antibody AMC-462, which belongs to the class $IgG_1$ and reacts with digestive system cancer, and to a method of detecting the presence of digestive system cancer.

The present invention is applicable in diagnosis of digestive system cancer, especially pancreatic cancer, and effective in the field of the diagnostic.

Carcinoembryonic antigen (CEA) has been hitherto known as a tumor marker of digestive system cancer. Methods of detecting the presence of digestive system cancer by measuring CEA using anti-CEA serum (polyclonal antibody) have been known. And methods of detecting the presence of digestive system cancer using anti-CEA monoclonal antibodies have also been developed. According to the serodiagnosis by measuring CEA, the positive rate is 30-60%, and thus it is unworthy of screening of digestive system cancer patients.

Recently, in the serodiagnosis using the monoclonal antibody NS19-9 which reacts with a colorectal cancer cell line, the positive rate for pancreatic cancer and bile duct cancer amounts to nearly 80%. And in the serodiagnosis using the monoclonal antibody DuPan-2 which reacts with a pancreatic cancer cell line, the positive rate for pancreatic cancer amounts to 60-70% [Chiryogaku 15, 484 (1985)].

As mentioned above, in the serodiagnosis using the monoclonal antibodies NS19-9 and DuPan-2, the positive rate for pancreatic cancer nearly amounts to 80%, but about 20% of negative results remains. Monoclonal antibodies which are effective in respect of the 20% of negative results, if available, would be very useful in the diagnosis of pancreatic cancer.

The present inventors have found that the monoclonal antibody AMC-462 produced by a hybridoma cell line between a spleen cell obtained from a mouse immunized with human gastric cancer tissue membrane preparations and a murine myeloma cell line has a strong reactivity with digestive system cancer, especially with pancreatic cancer, and is capable of detecting the presence of digestive system cancer in respect of the samples which give negative results in the serodiagnosis using NS19-9 or DuPan-2 and have completed the present invention based on the findings.

SUMMARY OF THE INVENTION

The invention thus provides an anti-human gastric cancer-reactive monoclonal antibody obtained by fusing spleen cells of a mouse immunized with human gastric cancer tissue membrane preparations and murine myeloma cell lines to generate hybridomas, selecting from among the hybridomas obtained a hybridoma clone producing a monoclonal antibody having specificity to human gastric cancer and cultivating the selected hybridoma in a medium or administering the hybridoma to a mouse to thereby cause hybridoma cell propagation in the ascitic fluid in the mouse, followed by separation, from the culture or ascitic fluid, of the antibody capable of recognizing sialylated glycoproteins or glycolipids as antigens.

BRIEF DESCRIPTION OF THE DRAWINGS

In the accompanying drawings,

FIG. 1 is a scatter chart showing the results of serodiagnosis of various diseases patients using AMC-462.

DESCRIPTION OF THE INVENTION

Figure 2:
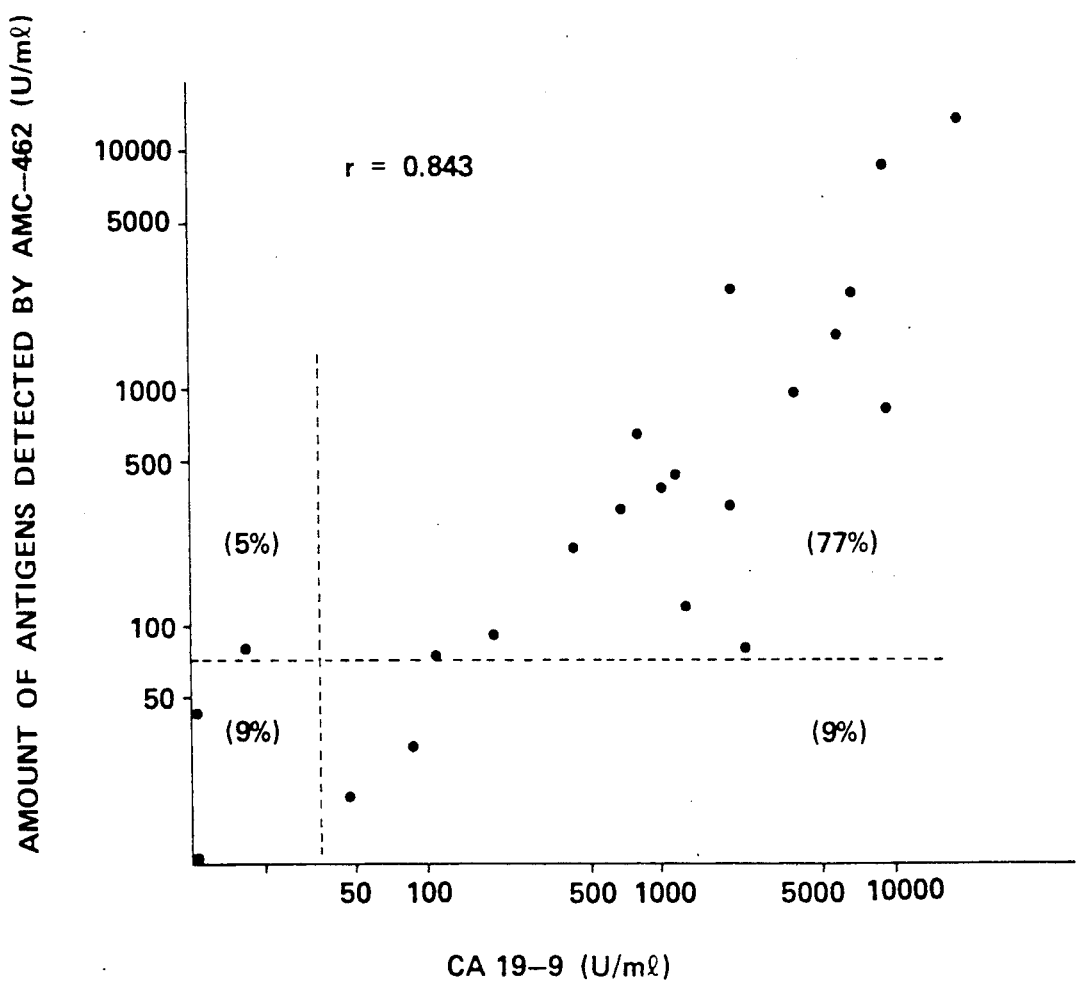
FIG. 2 is a graph showing the comparison of the amounts of CA19-9 in sera derived from pancreatic cancer patients with those of the antigens which are detected by AMC-462.

The monoclonal antibody according to the present invention belongs to the class $IgG_1$, reacts with digestive system cancer cells and recognizes sialylated glycoproteins or glycolipids as the antigen.

Cell line AMC-462 has been deposited at European Collection of Animal Cell Cultures as of May 8, 1986 under the Budapest Treaty (ECACC 86050801).

The monoclonal antibody according to the present invention is produced as follows.

(1) Immunization of animal and preparation of antibody-producing cells

Mice of 3-10 weeks of age, preferably 8-week-old mice, are immunized with human gastric cancer cells, tissues or membrane preparations derived from such tissues to cause mice to generate antibody-producing cells in the spleen, lymph node and peripheral blood. Mice that have immunological tolerance as a result of pretreatment with normal human stomach cells should preferably be used as the mice to be immunized. The immunization is generally performed by administering human gastric cancer cells ($10^6$ to $10^7$ cells per animal), human gastric cancer tissues, or membrane preparations (membrane fragments) derived from such tissues (10-500 μg per animal) together with an appropriate adjuvant (e.g. Freund's complete adjuvant, or aluminum hydroxide gel plus B. pertussis vaccine) to the animals subcutaneously, intravenously or intraperitoneally. Thereafter, the antigen administration is repeated 2-5 times at 1- to 2-week intervals. Three to seven days after each immunization, the blood is sampled from the eyeground venous plexus and the serum of each sample is tested as to whether it reacts with human gastric cancer by the enzyme immunoassay technique given below [Enzyme-linked Immunosorbent Assay (ELISA), published by Igaku Shoin, Tokyo 1976], for instance.

Normal human and tumor tissues are obtained from autopsies or surgical operations. The tissues are immediately frozen and stored at $-80°$ C. For membrane components the tissues are thawed at 4° C. in PBS containing 1 mM phenylmethyl sulfonyl fluoride. After mincing they are disrupted with an ultra disperser (LK-21; Yamato, Tokyo, Japan) and homogenized with a teflon-glass homogenizer. The homogenate is centrifuged at $100,000 \times g$, and then the pellet is resuspended at 1 mg protein in 1 ml of PBS and stored at $-80°$ C.

Enzyme immunoassay technique:

The membrane preparations of normal or tumor cells or tissues (membrane fragment fraction containing 10-1,000 μg of proteins per ml) are distributed into wells of a 96-well plate for EIA (product of Flow Laboratories) (100-200 μl per well). After allowing the membrane preparations to stand overnight to two overnights at 4° C., a supernatant is removed from the plate and, then, the plate is washed well with deionized water or phosphate-buffered saline (PBS; 1.83 g of disodium phosphate, 0.21 g of monopotassium phosphate and 7.65 g of sodium chloride in each liter of distilled water, pH 7.2). Then, 1% BSA (bovine serum albumin)-PBS is distributed into the wells (100-200 μl per well) and protein-binding sites remaining on each well are blocked by allowing the plate to stand overnight to two overnights at 4° C. After discarding the BSA-PBS, the wells are washed well with deionized water or PBS. Samples (mouse sera, hybridoma culture supernatants, or roughly purified monoclonal antibodies; each as the first antibody) are diluted with BSA-PBS and the dilutions are distributed into the wells (100 μl per well), followed by overnight standing at 4° C. After washing the wells once with deionized water and then 6 times with 2M NaCl solution, a 100-fold dilution of the rabbit anti-mouse immunoglobulin IgG-peroxidase conjugate (product of DAKO and distributed by Kyowa Medex; used as the second antibody) is distributed into the wells (100 μl per well). The plate is then allowed to stand at room temperature for 2 hours.

After washing well with PBS, an ABTS substrate solution [prepared by dissolving 550 mg of 2,2'-azinobis (3-ethylbenzothiazoline-6-sulfonic acid) diammonium salt in 1 liter of 0.1M citrate buffer (pH 4.2) and adding, just prior to use, hydrogen peroxide to a concentration of 1 μl/ml] is applied and the color developed is measured in terms of the absorbance $OD_{415nm}$. Those mice that strongly react with the gastric cancer cells, tissues or membrane preparations thereof are used as human gastric cancer-immunized mice, namely as sources of supply of antibody-producing cells for the hybridoma production.

When cells as such are used as the antigen in performing enzyme immunoassay, the target cells are cultivated on a Falcon 3072 plate, 0.25% glutaraldehyde-PBS is added and, after allowing it to stand at room temperature for 1-2 hours, the plate is washed well with PBS. Then, 100-200 μl of 1% BSA-PBS is added and, after 2 hours of standing, the plate is washed well with deionized water or PBS and submitted to antibody titer determination, which is conducted in the same manner as the case where an ordinary antigen-coated plate is used.

For submitting to cell fusion, human gastric cancer cells, tissues or membrane preparations are intraperitoneally administered to the immunized mice in a dose of 2 to $5 \times 10^6$ cells per animal or 20 to 400 μg per animal 3-4 days prior to the fusion treatment. The spleen is extirpated, cut into fragments in MEM (product of Nissui Pharmaceutical), loosened up with a pair of forceps, and centrifuged at 1,200 rpm for 5 minutes. The supernatant is discarded, and the sediment is deprived of erythrocytes by treatment with Tris-ammonium chloride buffer (pH 7.65) for 1-2 minutes, washed three times with MEM, and used as the spleen cells for fusion.

(2) Preparation of myeloma cells

A mouse-derived established myeloma cell line is used. Usable examples of such cell line include the 8-azaguanine resistant murine (BALB/c-derived) myeloma cell lines P3-X63Ag8-U1 (P3-U1) [Current Topics in Microbiology and Immunology-1] P3-NSI/1-Ag4.1 (NS-1) [European J. Immunology, 6, 511-519 (1976)], SP2/0-Ag14 (SP-2) [Nature, 276, 269-270 (1978)], P3-X63-Ag8 653 (653) [J. Immunology, 123, 1548-1550 (1979)] and P3-X63-Ag8 (X63) [Nature, 256, 495-497 (1975)]. The passage of these cell lines is performed in 8-azaguanine medium [normal medium prepared by adding, to RPMI-1640 medium, glutamine (1.5 mM), 2-mercaptoethanol ($5 \times 10^{-5}$M), gentamycin (10 μg/ml) and fetal calf serum (FCS; product of CSL) (10%), with further supplementation with 8-azaguanine (15 μg/ml)]. The cell line selected for cell fusion is transferred to normal medium 3-4 days before fusion to ensure the cell count of not less than $2 \times 10^7$ on the day of fusion.

(3) Cell fusion

The spleen cells prepared in (1) and the myeloma cells obtained in (2) are washed well with MEM or PBS, mixed in a cell number ratio of spleen cells: myeloma cells = 5 to 10:1 and then subjected to centrifugation (1,200 rpm, 5 minutes). The supernatant is discarded and the cell sediment is loosened up. With stirring at 37° C., a mixture of 2 g of polyethylene glycol 1000 (PEG-1000), 2 ml of MEM and 0.7 ml of dimethyl sulfoxide is added in an amount of 0.2-1 ml per $10^3$ spleen cells, and MEM is added until the whole volume is made up to be 50 ml after several additions of 1-2 ml of MEM at 1- to 2-minute intervals. After centrifugation (900 rpm, 5 minutes), the supernatant is discarded and the cell sediment is loosened gently. To the cells is added 100 ml of normal medium (RPMI-1640 with 10% FCS). The cells are suspended in the medium by gentle drawing up into the discharging from a measuring pipette.

The suspension obtained is distributed, in 1 ml-portions, into the wells of a 24-well incubation plate. Incubation is carried out in a 5% $CO_2$ incubator at 37° C. for 24 hours. HAT medium [normal medium supplemented with hypoxanthine ($10^{-4}$M), thymidine ($1.5 \times 10^{-5}$M) and aminopterine ($4 \times 10^{-7}$M)] is added to the incubation plate (1 ml per well) and incubation is conducted for a further 24 hours. Thereafter, 1 ml of the culture supernatant is discarded and the same volume of fresh HAT medium is added at 24-hour intervals for 2 days. The incubation in the $CO_2$ incubator at 37° C. is continued for 10-14 days.

For those wells in which fused cells grown and forming colonies are found, 1 ml of the supernatant is discarded and the same volume of HT medium (HAT medium minus aminopterine) is added, followed by medium replacement with fresh portions of HT medium at 24-hour intervals for 2 days.

After 3-4 days of cultivation in HT medium, a portion of the culture supernatant is collected and assayed for antibody titer relative to human gastric cancer by the above-mentioned enzyme immunoassay technique. Simultaneously, the reactivities with normal human cells or tissues and membrane preparations thereof, among others, are also determined by a similar method, and those wells for which selective reactivity with human gastric cancer cells or tissues or membrane preparations thereof is shown are selected. For the wells showing strong reactivity with human gastric cancer cells or tissues or membrane preparations thereof but no reactivity with normal human cells or tissues or membrane preparations thereof, among others, cloning is repeated twice by the limiting dilution technique. In this way, those clones for which high antibody titer values are stably obtainable relative to human gastric cancer cells or tissues or membrane preparations thereof are selected as anti-human gastric cancer monoclonal antibody-producing hybridoma cell lines.

(4) Preparation of monoclonal antibodies

Eight- to ten-week-old female C57BL/6 mice treated with pristane [intraperitoneally administered with 0.5 ml of 2,6,10,14-tetramethylpentadecane (pristane) and fed for 2 weeks] are intraperitoneally injected with the anti-human gastric cancer monoclonal antibody-producing hybridoma cells obtained in procedure (3) above at a dose of $2$–$4 \times 10^6$ cells per animal. In 10–21 days, the hybridoma cells produce ascites carcinoma in the mice. The ascitic fluid is collected from such mice, centrifuged (3,000 rpm, 5 minutes) to remove solids, subjected to salting out with 40% ammonium sulfate, dialyzed against 0.04M phosphate buffer (pH 8.0) supplemented with 0.03M NaCl, and passed through DE52 (product of Whatman) column. An $IgG_1$ fraction is collected and used as a purified monoclonal antibody.

The isotype of the antibody is determined by Ouchterlony's method (double immunodiffusion) [Seibutsukagaku Jikkenho (Methods in Experimental Biochemistry), vol. 15, Introduction to Experimental Immunology, p. 74, Gakkai Shuppan Center, 1981].

The quantity of protein is estimated by the Folin's method, followed by calculation based on the absorbance at 280 nm [1.4 ($OD_{280}$) approximately corresponds to 1 mg of immunoglobulin per ml].

The monoclonal antibodies thus obtained are evaluated for specificity characteristics based on (1) the reactivities with normal and tumor tissues and membrane preparations thereof derived from a variety of human organs obtained from a plurality of subjects, (2) the reactivities with a variety of normal human or tumor cell lines or human fetal cell line, or membrane preparations derived therefrom, (3) the reactivity with the hitherto known carcinoembryonic antigen (CEA) and (4) the reactivities with healthy human-derived and patient-derived sera, and the like as determined by an appropriate assay technique, such as the enzyme immunoassay method, fluorescent antibody method, immunohistological staining method (ABC method), etc. Those monoclonal antibodies that react with human gastric cancer and do not exhibit reactivity with the other antigens in any evaluation test are selected.

(5) Serodiagnosis

The serodiagnosis is performed as follows: A first antibody preparation (10–100 μg/ml) is distributed into the wells of a 96-well plate for EIA (50–200 μl per well). The plate is allowed to stand at 4° C. overnight to two overnights or at room temperature for 2–4 hours. After washing with PBS, 200 μl of BSA-PBS is added to each well, followed by further standing at 4° C. overnight or at room temperature for 2 hours. The plate is washed well with PBS, and 50–100 μl of a 1- to 100-fold dilution of a serum sample is added to each well. After allowing it to stand at 4° C. overnight or at room temperature for 2 hours, the plate is washed well with PBS. Then, a biotin- or peroxidase-labeled second antibody (10–100 μg/μl) is added to the wells (50–100 μl per well) and the plate is further allowed to stand at 4° C. overnight or at room temperature for 2–4 hours. When a biotin-labeled antibody is used as the second antibody, the plate is washed well with PBS, avidin-peroxidase or avidin-biotin-peroxidase (10 μg/ml) is added to the wells (50–100 μl per well), and the plate is allowed to stand at room temperature for 30 minutes and then washed well with PBS. Then, an ABTS substrate solution is added in an amount of 50–100 μl per well. After allowing the plate to stand at room temperature for 10–30 minutes, the reaction is terminated by adding 5% SDS solution in an amount of 50–100 μl per well. The $OD_{415}$ value is measured for each well and the quantity of the antigen in the serum sample is calculated based on the intensity of the color developed. By comparing the antigen levels in the sera of healthy humans with those in the sera of patients with various cancers, the normal level range is defined. When the level in question exceeds such a predetermined range, the test is regarded as positive.

(6) Antigen analysis

When, in performing the above-mentioned enzyme immunoassay, immunohistochemical staining or serodiagnosis, the antigens (gastric cancer membrane preparations, cultured gastric cancer cell lines, gastric cancer tissues) are pretreated with reagents such as enzymes (e.g. neuraminidase, protease) or periodic acid and then reacted with the monoclonal antibodies. The subsequent comparison for differences in reactivity with the monoclonal antibodies between the original antigens without such pretreatment and the antigens pretreated in the above manner can elucidate the chemical characteristics of the antigenic sites which the monoclonal antibodies recognize. That is, if the antigenicity disappears upon treatment with neuraminidase, it is assumed that sialic acids are associated with the antigenic determinants. If the antigenicity disappears upon treatment with protease, it is assumed that proteins are associated with the antigenic determinants. If the antigenicity disappears upon periodic acid treatment, sugar chains are presumably associated with the antigenic determinants.

The following examples illustrate the present invention in further detail.

EXAMPLE 1

(1) Preparation of antibody-producing cells

Normal human stomach tissue membrane preparations were administered intravenously to new-born C57BL/6 mice (purchased from Shizuoka Agricultural Cooperative Association for Laboratory Animals) within 24 postnatal hours at a dose of 1 mg of proteins per animal. After the lapse of 8 weeks, the mice were intraperitoneally administered with human gastric cancer membrane preparations (100 μg of proteins per animal) together with aluminum hydroxide gel (2 mg per animal) and killed B. pertussis vaccine ($1 \times 10^9$ per animal), followed by 3–5 immunizations with the same antigen without adjuvant at a dose of 100 μg per animal on the protein basis at 1- to 2-week intervals. From among these immunized mice, those mice whose antisera intensely reacted with human gastric cancer cells or tissues or membrane preparations derived therefrom were selected, and spleen cells were prepared from such mice and submitted to cell fusion.

(2) Preparation of myeloma cells

The 8-azaguanine-resistant murine myeloma cell line P3-U1 was cultivated in normal medium to thereby secure not less than $2 \times 10^7$ cells at the time of cell fusion, and submitted to cell fusion as a parent strain.

(3) Hybridoma production

The spleen cells and myeloma cells obtained in (1) and (2), respectively, were used in a ratio of 5:1 and subjected to fusion according to the procedure mentioned hereinabove. After cultivation in HAT medium at 37° C. under 5% $CO_2$ for 14 days, fused cells were selected and, after change of the medium to HT medium, cultivation was continued. Based on the results of anti-human gastric cancer antibody titer determination, active wells were selected and, after change of the medium to normal medium, cloning was repeated twice. The hybridoma cell line AMC-462 having no reactivity with normal human cells or tissues or other cancers and having specific reactivity with human gastric cancer, as determined by various assay methods, was thus selected.

(4) Monoclonal antibody purification

Pristane-treated 8-week-old female C57BL/6 mice were intraperitoneally injected with the hybridoma cell line AMC-462 obtained in (3) at a dose of $4 \times 10^6$ cells per animal. In 10-21 days, the hybridoma produced ascites carcinoma. The ascitic fluid was collected from ascitic fluid-bearing mice (5-10 ml per animal), deprived of solids by centrifugation (3,000 rpm, 5 minutes), subjected to salting out with 40% ammonium sulfate, dialyzed against 0.04M phosphate buffer (pH 8.0) supplemented with NaCl (0.03M), and passed through a DE52 (product of Whatman) column (bed volume 50 ml) at a flow rate of 20-30 ml/hr. An $IgG_1$ fraction was collected and used as purified antibody.

(5) Specificity of AMC-462

The results of testing of the thus-obtained anti-human gastric cancer-reactive monoclonal antibody AMC-462 for reaction specificity expressed a fraction of positive reactions over the number of tests conducted, are summarized below in Table 1.

The measurement was performed by enzyme-linked immunosorbent assay (ELISA) as follows.

In the case of membrane preparations from tissues as a target, a solution of 0.1 mg/ml membrane preparations from tissues was distributed in 50 μl portions into the wells of a 96-well plate for EIA (purchased from Limbro). After allowing it to stand at 37° C. for 2 hours or at 4° C. overnight, the plate in which the membrane preparations from tissues had been fixed was washed with PBS. Then PBS supplemented with 10% fetal calf serum was distributed into the wells (100 μl per well). The plate in which the active residues of the fixed membrane preparations from tissues had been protected was washed with PBS. The first antibody (AMC-462) was distributed into the wells (50 μl per well), followed by allowing the plate to stand at 37° C. for 1-2 hours or at 4° C. overnight to carry out the reaction between the target and the antibody.

After washing five times with PBS supplemented with 0.05% Tween-20 (purchased from Wako Pure Chemicals) to remove the unreactive antibodies, peroxidase-labeled rabbit anti-mouse immunoglobulin (purchased from Miles-Yeda; 200-fold dilution) as the second antibody was distributed into the wells (50 μl per well), and the reaction was carried out at 37° C. for 1 hour. After washing five times with PBS supplemented with 0.05% Tween-20 and three times with deionized water, the ABTS substrate solution was added (50 μl per well) and the reaction was allowed to proceed and then terminated by adding 5% sodium dodecyl sulfate solution (50 μl per well).

In the case of cultivated cell lines as a target, the cell lines were cultivated in the wells of a 96-well plate for cultivation (purchased from Limbro). After the cells were confluent in the plate, the immune reaction was allowed to proceed in a similar manner to the case of the membrane preparations from tissues described above except that the reactions of the first antibody and of second antibody concerned were respectively carried out at room temperature for 30 minutes. After the color development, the reaction was terminated by transferring the reaction mixture into a 96-well plate for analysis.

In the case of CEA, the immune reaction was carried out in a similar manner to the case of the membrane preparations from tissues except that CEA instead of the membrane preparations from tissues was used.

For each case, the absorbance at 415 nm was measured, putting the absorbance at 490 nm as the control.

TABLE 1

| Binding activity (ELISA) | | | Antibody AMC-462 |
|---|---|---|---|
| | Membrane preparations from tissues | Gastric cancer | 6/7 |
| | | Pancreatic cancer | 4/4 |
| | | Colorectal cancer | 2/4 |
| | | Tissues derived from normal stomach | 0/6 |
| | Cultured cell lines | Gastric cancer | 4/5 |
| | | Pancreatic cancer | 2/2 |
| | | Colorectal cancer | 3/4 |
| | | Lung cancer | 1/5 |
| | | Fetal skin | 0/1 |
| | Antigen | CEA | 0/1 |

As shown in Table 1, AMC-462 is reactive with not only gastric cancer but also digestive system cancer such as pancreatic cancer, colorectal cancer, etc. But since AMC-462 is non-reactive with CEA, AMC-462 is different from anti-CEA antibody. The results indicate that it is possible to make a pathologic diagnosis of digestive system cancer by immunohistochemical staining using AMC-462.

EXAMPLE 2

A suspension of AMC-462 (10 μg/ml) was distributed in 50-μl portions into the wells of a 96-well plate for ELISA (purchased from Flow Laboratories). After allowing it to stand overnight at 4° C., the plate was washed with PBS. Then, 1% BSA-PBS was added (200 μl per well). After overnight standing, the plate was washed well with PBS. To the plate were added 5-fold dilutions of healthy human-derived sera (85 samples), gastric cancer patient-derived sera (86 samples), pancreatic cancer patient-derived sera (22 samples), hepatoma patient-derived sera (15 samples), colon cancer patient-derived sera (16 samples), rectal cancer patient-derived sera (12 samples), gall bladder cancer patient-derived sera (20 samples), breast cancer patient-derived sera (3 samples), benign gastrointestinal disease patient-derived sera (21 samples), benign pancreatic disease patient-derived sera (38 samples), benign gall bladder disease patient-derived sera (11 samples) or liver cirrhosis patient-derived sera (3 samples) in an amount of 50 μl per well. After overnight standing at 4° C., the plate was washed well with PBS. Then, biotin-labeled anti-gastric cancer monoclonal antibody AMC-462 (10 μg/ml) was added as the second antibody (100 μl per well). The plate was allowed to stand overnight at 4° C. and, then, washed well with PBS. Avidin-biotin-peroxidase (product of Vector) (10 μg/ml) was distributed in 100 μl-portions into the wells, and the plate was allowed to stand at room temperature for 1 hour and then washed with PBS. Thereafter, the ABTS substrate solution was added in an amount of 100 μl per well and the reaction was allowed to proceed at room temperature for 30 minutes and then terminated by adding 5% SDS solution (100 ul per well). For each well, the color development was measured by an absorptiometer ($OD_{415}$). As shown in FIG. 1, no positive result ($OD_{415}$ cutoff value ±7SD) was obtained for the 85 serum samples (0%) from healthy subjects, whereas, for the serum samples from gastric cancer patients, 16 out of 86 samples (18.6%) gave positive results, for the serum samples from pancreatic cancer patients, 18 out of 22 samples (81.8%) gave positive results, for the serum samples from hepatoma patients, 5 out of 15 samples (33.3%) gave positive results, for the serum samples from colon cancer patients, 1 out of 16 samples (6.7%) gave positive results, for the serum samples from rectal cancer patients, none of 12 samples (0%), for the serum samples from gall bladder cancer patients, 8 out of 20 samples (40%), for the serum samples from breast cancer patients, 1 out of 3 samples (33.3%). As for benign diseases patients, none of 21 serum samples from gastrointestinal disease patients gave positive results (0%), for the serum samples from benign pancreatic disease patients, one out of 38 samples (2.6%), for the serum samples from benign gall bladder disease patients, none of 11 samples (0%) and for the serum samples from liver cirrhosis patients, none of 3 samples (0%). Thus, the positive rate was extremely low. This result shows that the present serodiagnosis system using AMC-462 is highly effective in serodiagnosis of digestive system cancer, especially pancreatic cancer.

EXAMPLE 3

The amounts of CA19-9 (antigen defined by NS19-9) and DuPan-2 (antigen defined by DuPan-2), which were known markers of pancreatic cancer, in the same serum samples as those derived from pancreatic cancer patients, used in Example 2 were measured.

FIG. 2 shows the comparison of the amounts of CA19-9 with the amounts of the antigen defined by the monoclonal antibody AMC-462 according to the present invention in the same serum samples.

Figure 3:
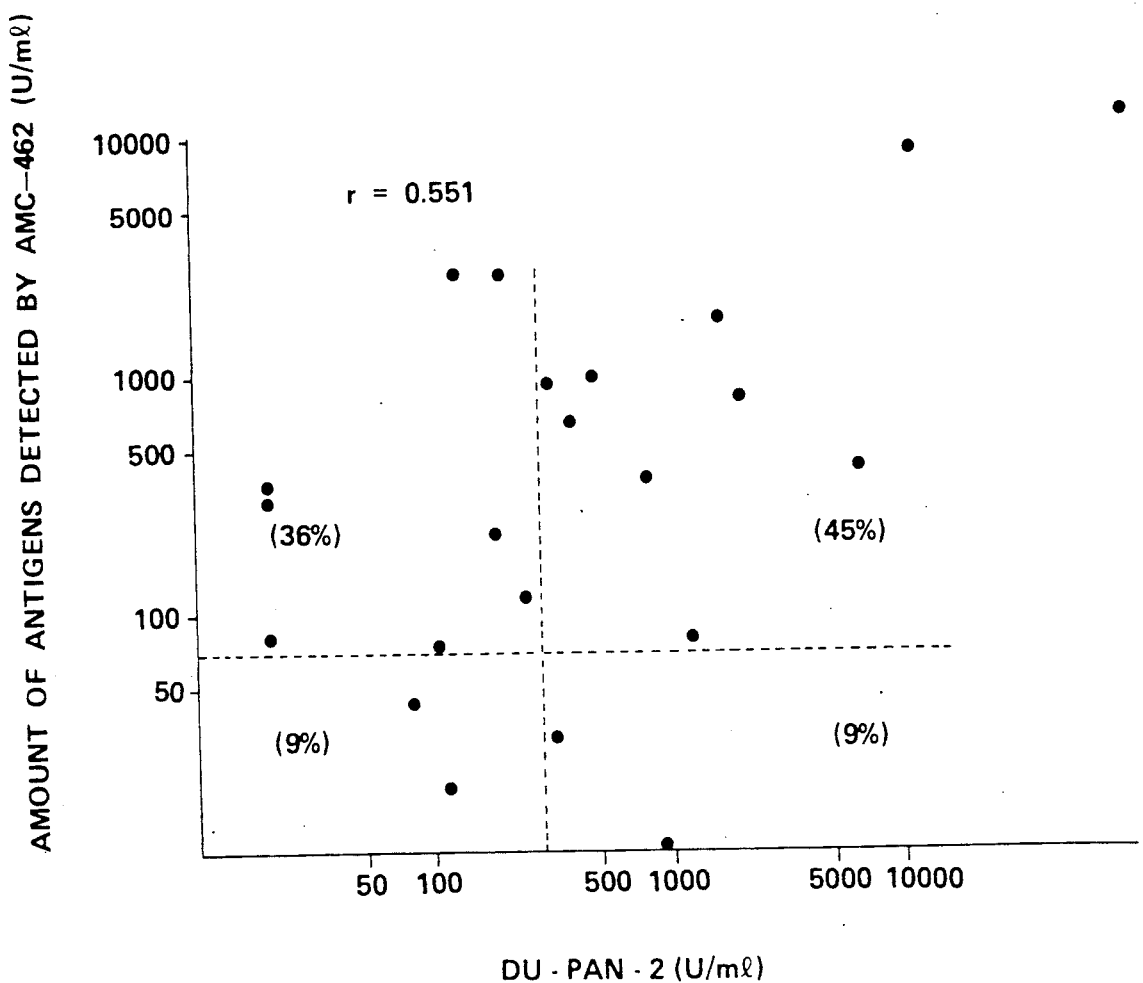
FIG. 3 is a graph showing the comparison the amount of DuPan-2 in sera derived from pancreatic cancer patients with those of the antigens which are detected by AMC-462.

FIG. 3 shows the comparison between the amounts of the antigen defined by DuPan-2 and the amounts of the antigen defined by AMC-462 in the same serum samples.

As apparent from FIG. 2, the amounts of antigen in the serum samples from pancreatic cancer patients measured by the serodiagnosis system using AMC-462 of the present invention highly correlate with the amounts of CA19-9. But, 5% of the samples which gives negative results for CA19-9 gives positive results in the serodiagnosis system using AMC-462.

FIG. 3 indicates that the amounts of the antigens of cancer defined by the present invention little correlate with the amounts of DuPan-2. From the point of view of the positive rate, AMC-462 can be more effective for serodiagnosis of pancreatic cancer than DuPan-2.

EXAMPLE 4

The results obtained in Examples 1 and 3 indicate that the antigen detectable in the serodiagnosis system using AMC-462 was different from CEA and DuPan-2 which were known tumor markers of digestive system cancer, especially pancreatic cancer. In order to more definitely investigate the difference from CA19-9, the binding test was carried out by the method of sandwich ELISA.

That is, suspensions of AMC-462 or NS19-9 (10 μg/ml) as the first antibody were distributed into the wells of a 96-well plate for EIA (50 μl/well) and fixed on the bottom of the well. The plate was blocked by 1% BSA-PBS and then the serum samples from pancreatic cancer patients containing both the antigen defined by CA19-9 and the antigen defined by AMC-462 were added in an amount of 50 μl per well. After well washing, the monoclonal antibody NS19-9 or AMC-462 (0.1-50 μg/ml) was added as an inhibiting antibody and the plate was washed well. Then, the biotin-labeled monoclonal antibody NS19-9 or biotin-labeled monoclonal antibody AMC-462 was added as the second antibody and the plate was washed well. Avidin-biotin-peroxidase was distributed into the wells and then the plate was washed well. Thereafter, the ABTS substrate solution was added and an enzyme reaction was allowed to proceed and then terminated by adding SDS solution. For each well, the absorbance at 415 nm was measured.

Figure 4:
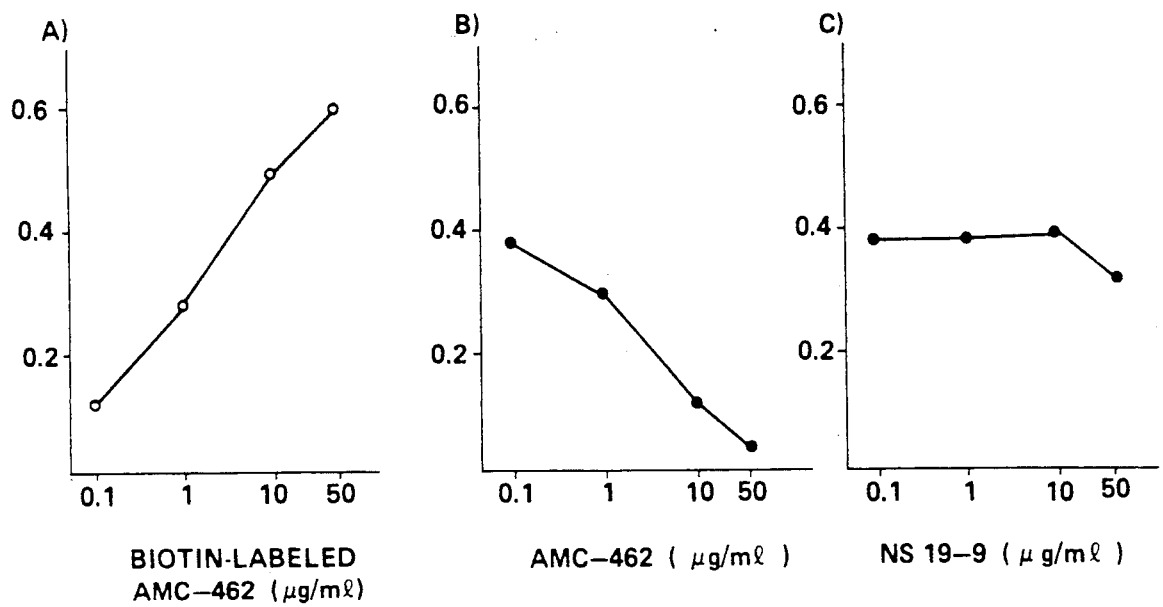
FIG. 4 are graphs showing the results of inhibiting tests of AMC-462 to NS19-9.
Figure 4:
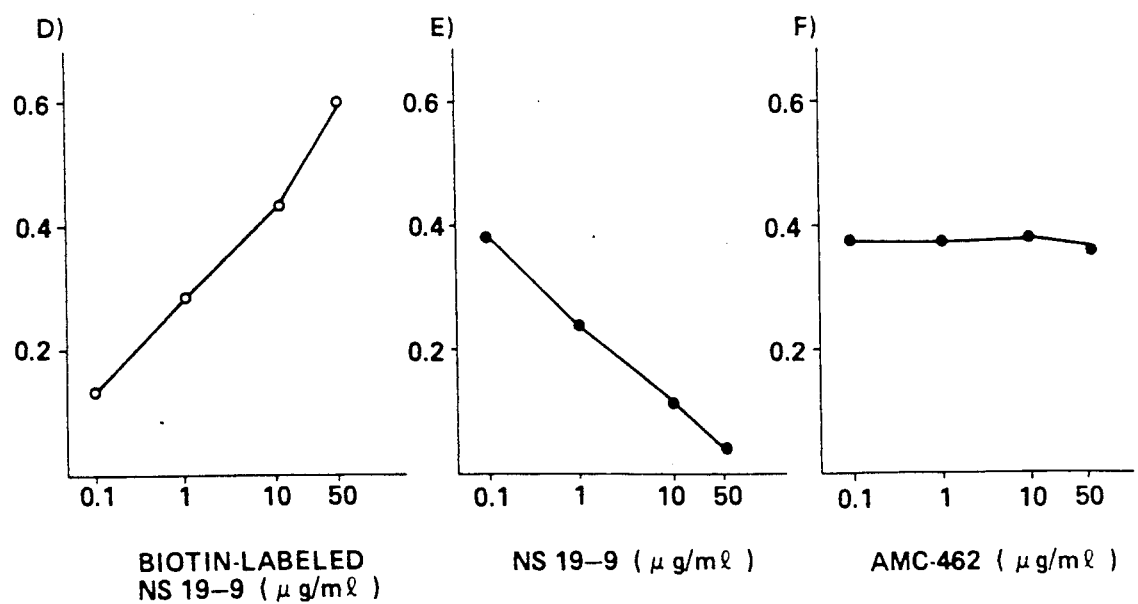

The result was shown in FIG. 4. In FIG. 4, cases A, B, C, D, E and F mean the following combinations.

| (A) | the first antibody | AMC-462 (10 μg/ml) |
|---|---|---|
|   | the second antibody | biotin-labeled AMC-462 (0.1-50 μg/ml) |
|   | inhibiting antibody | none |
| (B) | the first antibody | AMC-462 (10 μg/ml) |
|   | the second antibody | biotin-labeled AMC-462 (10 μg/ml) |
|   | inhibiting antibody | AMC-462 (0.1-50 μg/ml) |
| (C) | the first antibody | AMC-462 (10 μg/ml) |
|   | the second antibody | biotin-labeled AMC-462 (10 μg/ml) |
|   | inhibiting antibody | NS19-9 (0.1-50 μg/ml) |
| (D) | the first antibody | NS19-9 (10 μg/ml) |
|   | the second antibody | biotin-labeled NS19-9 (0.1-50 μg/ml) |
|   | inhibiting antibody | none |
| (E) | the first antibody | NS19-9 (10 μg/ml) |
|   | the second antibody | biotin-labeled NS19-9 (10 μg/ml) |
|   | inhibiting antibody | NS19-9 (0.1-50 μg/ml) |
| (F) | the first antibody | NS19-9 (10 μg/ml) |
|   | the second antibody | biotin-labeled NS19-9 (10 μg/ml) |
|   | inhibiting antibody | AMC-462 (0.1-50 μg/ml) |

As apparent from FIG. 4, the reactivity of NS19-9 and AMC-462 was completely inhibited by NS19-9 and AMC-462, respectively, and that of NS19-9 was not inhibited by AMC-462 and that of AMC-462 was not by NS-19-9. Therefore, it is assumed that the antigens recognized by AMC-462 are different from those recognized by NS19-9.

While the invention has been described in detail and with reference to specific embodiment thereof, it will be apparent to one skilled in the art that various changes and modifications can be made therein without departing from the spirit and scope thereof.

What is claimed is:

1. An anti-human gastric cancer monoclonal antibody, produced by hybridoma cell line AMC-462 (ECACC 86050801), which belongs to the class $IgG_1$, reacts with sialylated glycoproteins or glycolipids derived from digestive system cancer-associated antigens and is non-reactive with normal stomach tissue.

2. Murine hybridoma cell line AMC-462 (ECACC 86050801).

3. A serodiagnostic method of detecting the presence of human digestive system cancer antigen specifically recognized by monoclonal antibody AMC-462 (ECACC 86050801) defined in claim 1 comprising:
   (1) reacting a serum sample from a patient suspected to contain digestive system cancer the antigen with monoclonal antibody AMC-462;
   (2) removing excess antigen from the reaction;
   (3) adding a second, labeled antibody specific for the antigen; and
   (4) quantitating the bound, labeled antibody as a determination of the presence of human digestive system cancer.

4. The serodiagnostic method according to claim 3, wherein the digestive system cancer is selected from the group consisting of gastric cancer, pancreatic cancer and colorectal cancer.

5. The method according to claim 3, wherein the immunoassay is a sandwich-type enzyme immunoassay method.

6. An immunohistochemical staining method for determining the presence of human digestive system cancer cells, which comprises applying to a tissue sample from the digestive system of a patient suspected of having digestive system cancer a staining amount of the antibody defined in claim 1, and examining the thus-treated tissue sample to determine the selective reaction of the antibody with digestive system cancer cells and the absence of a reaction with the cells of normal human stomach tissue or cells.

* * * * *

UNITED STATES PATENT AND TRADEMARK OFFICE
CERTIFICATE OF CORRECTION

PATENT NO. : 5,051,355

DATED : September 24, 1991

INVENTOR(S) : HAJIME YOSHIDA, ET AL.

It is certified that error appears in the above-identified patent and that said Letters Patent is hereby corrected as shown below:

COLUMN 10

Line 67, "class $IgG_1.,$" should read --class $IgG_1,$--.

COLUMN 11

Line 10, "digestive system cancer the" should read --the digestive system cancer--.

Signed and Sealed this

Third Day of March, 1992

Attest:

Attesting Officer

HARRY F. MANBECK, JR.

Commissioner of Patents and Trademarks